US00PP25883P2

(12) United States Plant Patent
Ault

(10) Patent No.: US PP25,883 P2
(45) Date of Patent: Sep. 8, 2015

(54) ***PHLOX* PLANT NAMED 'PINK PROFUSION'**

(50) Latin Name: *Phlox×procumbens*
Varietal Denomination: Pink Profusion

(71) Applicant: James R. Ault, Libertyville, IL (US)

(72) Inventor: James R. Ault, Libertyville, IL (US)

(73) Assignee: CHICAGOLAND GROWS, INC, Glencoe, IL (US)

( * ) Notice: Subject to any disclaimer, the term of this patent is extended or adjusted under 35 U.S.C. 154(b) by 113 days.

(21) Appl. No.: 13/998,943

(22) Filed: Dec. 23, 2013

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Susan McCormick Ewoldt
(74) *Attorney, Agent, or Firm* — Penny J. Aguirre

(57) ABSTRACT

A new cultivar of *Phlox* plant, 'Pink Profusion', that is characterized by its dense low mounded plant habit with upright to lax flowering stems borne about 10 cm above the semi-evergreen basal foliage, its very large 2.8 cm wide flowers with that are deep purple-pink in color, its broad petals that consistently overlap for at least three-quarters of their length, and its pair of distinct, broad, red-purple colored striae on each petal that are bounded by a conspicuous off-white halo at the base of the petals.

2 Drawing Sheets

Botanical classification: *Phlox×procumbens.*
Cultivar designation: 'Pink Profusion'.

BACKGROUND OF THE INVENTION

The present invention relates to a new and distinct cultivar of *Phlox* plant, botanically known as *Phlox×procumbens* 'Pink Profusion' and will be referred to hereafter by its cultivar name, 'Pink Profusion'. The new cultivar represents a new herbaceous perennial grown for landscape use.

The new invention arose from an ongoing controlled breeding program by the Inventor in Glencoe, Ill. The new invention arose from an ongoing controlled breeding program by the Inventor in Glencoe, Ill. The objectives of the breeding program are to develop improved cultivars of spring blooming moss *phlox* by developing select interspecific hybrids of *Phlox* with novel traits of flower colors, plant habits, and tolerance to drought and soils with high salinity and pH.

'Pink Profusion' was derived from a cross made in May of 2007 under controlled conditions (that excluded natural pollinators) between *Phlox subulata* 'McDaniels's Cushion' (not patented) as the female parent and pollen that was pooled from multiple unnamed plants of *Phlox stolonifera* as the male parent. The resulting seedlings were planted for evaluation in June of 2008. 'Pink Profusion' was selected in May of 2009 as a single unique plant amongst the resulting seedlings.

Asexual propagation of the new cultivar was first accomplished by stem tip cuttings by the Inventor in June of 2009 in Glencoe, Ill. Asexual propagation by stem tip cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Pink Profusion' as a unique cultivar of *Phlox*.

1. 'Pink Profusion' exhibits a dense low, mounded plant habit with upright to lax flowering stems borne about 10 cm above the semi-evergreen basal foliage.
2. 'Pink Profusion' exhibits very large 2.8 cm wide flowers with that are deep purple-pink in color (larger than any flowers of this hybrid known to the Inventor).
3. 'Pink Profusion' exhibits flowers with broad petals that consistently overlap for at least three-quarters of their length.
4. 'Pink Profusion' exhibits flowers with a pair of distinct, broad, red-purple colored striae on each petal that are bounded by a conspicuous off-white halo at the base of the petals.

The female parent of 'Pink Profusion', 'McDaniel's Cushion', differs from 'Pink Profusion' in having flowers that are deep pink in color, in having diffused deep rose pink striae on each petal and no halo, and in having smaller needle-like leaves. The male parent of 'Pink Profusion' an unnamed plant of *Phlox stolonifera* differs from 'Pink Profusion' in having inflorescences that grow taller above the vegetative shoots (an average of 15 to 25 cm), in having larger, spatulate shaped basal leaves, in having a low, open vegetative, spreading plant habit, and in having distinctly fragrant flowers. 'Pink Profusion' can also be most closely compared to the *Phlox×procumbens* cultivars 'Variegata' (not patented) and 'Rosea' (not patented). Both cultivars are similar to 'Pink Profusion' in having mounded plant habits with upright to lax flowering stems borne about 10 cm above the semi-evergreen basal foliage. 'Variegata' differs from 'Pink Profusion' in having leaves that are variegated, in having smaller flowers, and in having dispersed, faint purple striae with no adjacent halo. 'Rosea' differs from 'Pink Profusion' in having smaller flowers that are lilac pink in color, in having very faint, indistinct striae with no adjacent halo, and in having narrower petals that overlap for only one third of their length.

BRIEF DESCRIPTION OF THE DRAWINGS

The accompanying colored photographs illustrate the overall appearance and distinct characteristics of the new *Phlox*.

The photographs were taken of two year-old plants of 'Pink Profusion' as grown in a trial garden in Glencoe, Ill.

Figure 1:
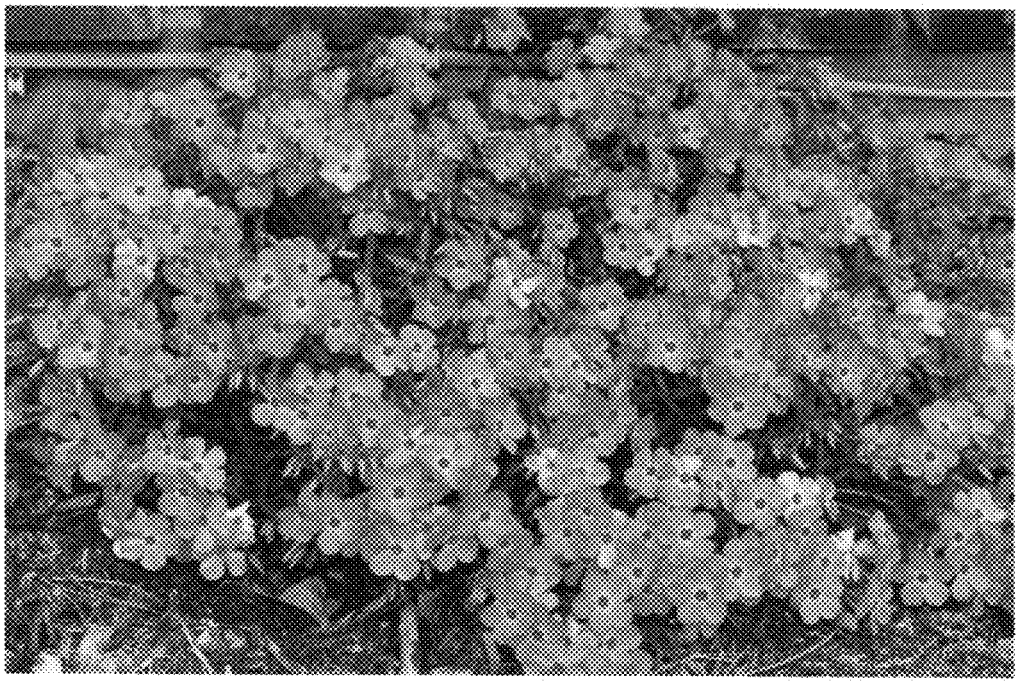

The photograph in FIG. 1 provides an overall view of the plant habit of 'Pink Profusion' in bloom.

Figure 2:
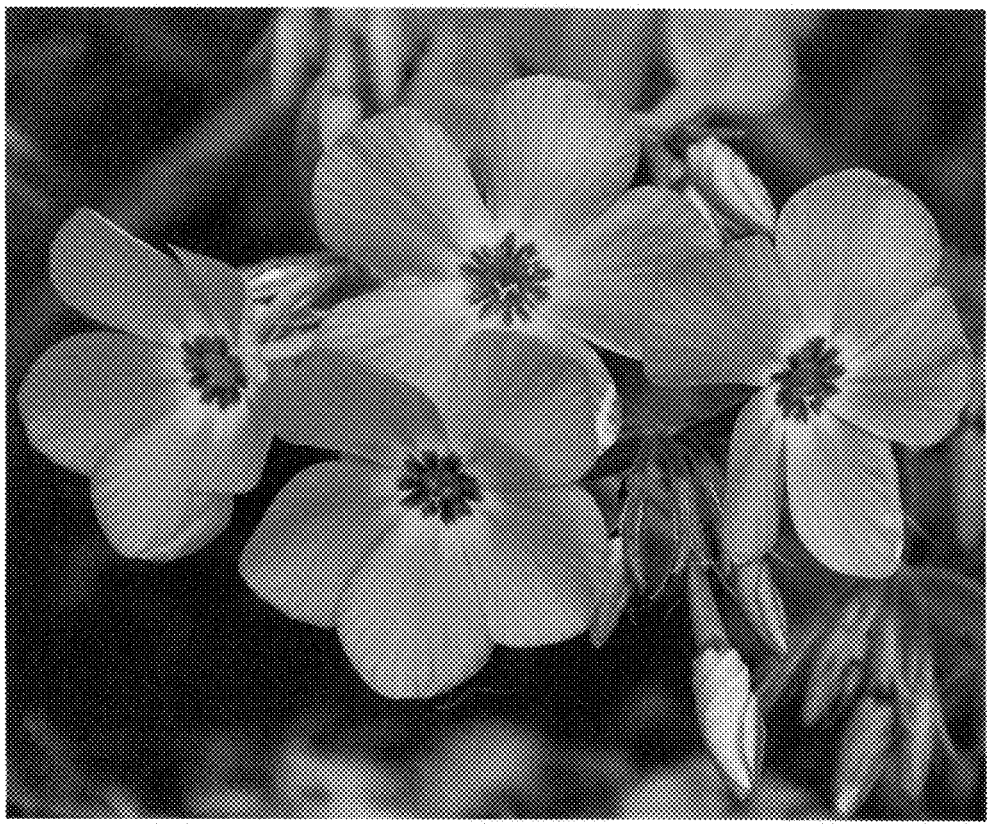

The photograph in FIG. 2 provides a close-up view of the flowers of 'Pink Profusion'.

The colors in the photograph may differ slightly from the color values cited in the detailed botanical description, which accurately describe the colors of the new *Phlox*.

DETAILED BOTANICAL DESCRIPTION OF THE PLANT

The following is a detailed description of two year-old plants of the new cultivar as grown in a trial garden in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms for four to five weeks beginning in mid to late April and continuing into early June in northern Illinois.

*Plant habit.*—Low, mounded plant habit with upright to lax flowering stems borne about 10 cm above the semi-evergreen basal foliage.

*Height and spread.*—An average of 13 cm in height (in bloom) and 33 cm in width, foliage height is an average of 3 cm with blooms held an average of 10 cm above the basal foliage.

*Hardiness.*—At least hardy in U.S.D.A. Zones 5 to 7.

*Diseases and pests.*—Good resistance to powdery mildew has been observed.

*Root description.*—Fibrous.

*Growth rate.*—Vigorous.

*Propagation.*—Stem tip cuttings.

Stem description:

*Stem size.*—An average of 9 cm in length and 2 mm in width, with lateral stems an average of 7 cm in length and 2 mm in width.

*Stem shape.*—Oval.

*Stem strength.*—Strong.

*Stem color.*—144B.

*Stem surface.*—Slightly glossy, covered with wooly dense pubescent hairs about 1 mm in length.

*Stem aspect.*—Held upright to lax.

*Internode length.*—An average of 1 cm.

*Branching habit.*—An average of 20 stems per plant, an average of 2 lateral branches per main stem.

Foliage description:

*Leaf shape.*—Narrowly elliptic to linear.

*Leaf division.*—Simple.

*Leaf base.*—Attenuate.

*Leaf apex.*—Acute acuminate.

*Leaf venation.*—Pinnate, not conspicuous, matches leaf color on upper and lower surfaces.

*Leaf margins.*—Entire.

*Leaf attachment.*—Sessile.

*Leaf arrangement.*—Opposite.

*Leaf surface.*—Glabrous, dull and sparsely covered in fine pubescence 1 mm in length on upper and lower surface.

*Leaf color.*—Upper and lower surface newly formed; 144B, upper surface mature; 144A, lower surface mature; 146B.

*Leaf size.*—Cauline leaves, an average of 2.5 cm in length and 6 mm in width, basal leaves; an average of 3.4 cm in length and 6 mm in width.

*Leaf quantity.*—An average of 16 on a stem.

*Leaf fragrance.*—None.

Flower description:

*Inflorescence type.*—Compound panicle on terminus of main stems and lateral branches.

*Lastingness of inflorescence.*—About 3 to 4 weeks from the opening of the first flower to senescence of last flower, individual flower lasts about 5 days.

*Inflorescence size.*—An average of 4 cm in height and 8 cm in diameter.

*Flower fragrance.*—Faint to none.

*Flower number.*—Up to 9 per terminal inflorescence, and 3 per lateral stems.

*Flower aspect.*—Upright to outward, dependent on location on the inflorescence.

*Flower bud.*—Average of 3 cm in length and up to 4 mm in width, conical in shape petal portion is a blend of 75A and 75B in color, calyx portion is 143A in color.

*Flower form.*—Explanate with tubular base.

*Flower size.*—An average of 2 cm in height and 2.8 cm in diameter.

*Corolla tube.*—About 1 cm in length, 2 mm in width, 75C in color, glabrous and satiny surface.

*Corolla lobes.*—5, orbicular-obovate in shape, held nearly horizontally when fully open, slightly overlapping, about 8 mm in length and width, apex rounded, base broadly cuneate and fused to tube, entire margins, upper surface color when opening and mature a blend of 75A and 75B with a distinct pair of striae N79B near base and a halo at base N155C, lower surface color when first opening and maturing a blend of 75C and 75D, glabrous on upper and lower surface.

*Calyx.*—Campanulate in form, comprised of fused sepals with lanceolate shaped sepal tips free, an average of 1 cm in length and 3 mm in width.

*Sepals.*—5, primarily fused with free tips, linear in shape, margins entire, base fused (about 80%), apex narrowly apiculate, an average of 7 mm in length and 1 mm in width, inner and outer surface is sparsely puberulent, color on upper and lower surface; 143A.

*Peduncles.*—Oval in shape, primary an average of 2.5 cm in length and 1 mm in width, secondary an average of 1.5 cm in length and 1 mm in width, primary held upright, secondary held at about a 45° angle, satiny and sparsely puberulent surface, color of base to midsection 145A, peduncle leaves; an average of 2 pairs, an average of 1 cm in length and 2 mm in width, all other characteristics match stem leaf characteristics.

*Pedicels.*—Oval in shape, an average of 3 mm in length and 1 mm in width, sparsely pubescent surface, color 147A.

Reproductive organs:

*Gynoecium.*—1 pistil, stigma is 1 mm in length and 150C in color, style is about 1.5 cm in length, very fine and 155A in color, ovary is inferior, oblong in shape, about 1 mm in length and 1 mm in width and 149A in color.

*Androcoecium.*—4 stamens, anthers are basifixed, oblong in shape, 2 mm in length and 17A in color, filaments are adnate to petals, 1 cm in length and 155B in color, pollen is low in quantity and 17A in color.

*Seeds.*—Seed production has never been observed, presumed to be sterile.

It is claimed:

1. A new and distinct cultivar of *Phlox* plant named 'Pink Profusion' as herein illustrated and described.

* * * * *